(12) United States Patent
Begelman et al.

(10) Patent No.: US 11,921,058 B2
(45) Date of Patent: Mar. 5, 2024

(54) IMAGING SYSTEM AND DATA ACQUISITION METHOD AND STRUCTURE THEREOF

(71) Applicant: CANON MEDICAL SYSTEMS CORPORATION, Tochigi (JP)

(72) Inventors: James Lawrence Begelman, Evanston, IL (US); Kevin Zimmerman, Sturtevant, WI (US); Thomas Labno, Palatine, IL (US); John Baumgart, Hoffman Estates, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 107 days.

(21) Appl. No.: 17/499,720

(22) Filed: Oct. 12, 2021

(65) Prior Publication Data

US 2023/0111828 A1 Apr. 13, 2023

(51) Int. Cl.
*G01N 23/046* (2018.01)
*A61B 6/00* (2006.01)
*A61B 6/03* (2006.01)

(52) U.S. Cl.
CPC .......... *G01N 23/046* (2013.01); *A61B 6/032* (2013.01); *A61B 6/4233* (2013.01); *A61B 6/54* (2013.01);
(Continued)

(58) Field of Classification Search
CPC ........ G01T 1/2985; G01T 1/17; G01T 1/247; G01T 1/1663; G01T 1/246; G01T 1/24; G01T 1/18; G01T 1/161; G01T 1/366; A61B 6/4241; A61B 6/032; A61B 6/56; A61B 6/54; A61B 6/4233; A61B 6/4266; A61B 6/037; A61B 6/482; A61B 6/42; A61B 6/4208; A61B 6/52; A61B 6/4435; A61B 6/582; A61B 6/5205; A61B 6/4452; A61B 6/4441; A61B 6/4028; A61B 6/14; A61B 6/035; A61B 6/4476; A61B 6/4085; A61B 6/025; A61B 34/20; A61B 17/1764;
(Continued)

(56) References Cited

U.S. PATENT DOCUMENTS 9,964,650 B2 5/2018 Cho
10,396,109 B2 8/2019 Iniewski et al.
(Continued)

FOREIGN PATENT DOCUMENTS

GB 2600550 A * 5/2022 ........... G06K 9/6256
WO 2010062465 A1 6/2010

*Primary Examiner* — Irakli Kiknadze
(74) *Attorney, Agent, or Firm* — Canon U.S.A., Inc. IP Division

(57) ABSTRACT

A computer-tomography (CT) imaging system, comprising an imaging data acquisition system. The imaging data acquisition system includes a plurality of sets of a detector section, a storage section, and an aggregation section. The detector section includes a plurality of detector elements each being configured to convert radiation into electric signals. The aggregation section is configured to aggregate imaging data carried by the electronic signals from the detector section. The storage section is connected with an output of the detector section and an input of the aggregation section. The storage section comprises a predetermined number of non-volatile memories to store the imaging data from the corresponding detector elements.

22 Claims, 7 Drawing Sheets

(52) U.S. Cl.
CPC .......... *A61B 6/56* (2013.01); *G01N 2223/304* (2013.01)

(58) Field of Classification Search
CPC ....... A61B 34/25; A61B 90/361; A61B 90/37; A61B 34/32; A61B 6/4411; A61B 6/04; A61B 6/027; A61B 6/102; A61B 6/46; A61B 6/501; A61B 6/469; A61B 6/463; A61B 6/145; A61B 8/5276; A61B 6/5264; A61B 6/5294; A61B 8/5207; A61B 6/5211; G01N 23/046; G01N 2223/501; G01N 2223/3303; G01N 2223/304; G01N 2223/50; G01N 23/02; H04N 5/32; H04N 25/75; G21K 2207/00; H05G 1/00; H03K 19/17716; H03K 5/135; H03K 23/40; H01L 27/14609; G06T 1/60; G06T 7/0012; G06T 2207/10081; G06T 2207/10116; G06T 1/0007; G06T 3/40; G06T 17/00; G06T 7/80; G06T 2207/30004; G06T 2207/10112; G06T 2207/20081; G06T 2207/20061; G06T 2207/20084; G06T 11/008; G06T 11/006; G06T 7/215; G06T 7/254; G01V 5/005; G16H 30/40; G16H 50/70; G16H 20/40; G16H 30/20; G06N 3/08; A61N 5/1048; A61N 5/1071; A61N 5/103
USPC .......................................... 378/4, 15, 19, 62
See application file for complete search history.

(56) References Cited

U.S. PATENT DOCUMENTS

| | | | |
|---|---|---|---|
| 10,743,826 B2 | 8/2020 | Cao et al. | |
| 2003/0206609 A1* | 11/2003 | Kling | G06T 1/20 378/4 |
| 2012/0195403 A1* | 8/2012 | Vedantham | A61B 6/022 378/62 |
| 2014/0009573 A1* | 1/2014 | Fujita | A61B 6/14 348/36 |
| 2015/0190107 A1* | 7/2015 | Kim | A61B 6/032 600/407 |
| 2017/0000675 A1* | 1/2017 | Hight | A61B 6/0407 |
| 2018/0193667 A1* | 7/2018 | Kaiser | A61N 5/1049 |
| 2018/0217271 A1* | 8/2018 | Cho | G01T 1/247 |
| 2019/0104940 A1* | 4/2019 | Zhou | A61B 5/0035 |
| 2022/0036605 A1* | 2/2022 | Riddell | A61B 6/4208 |
| 2022/0232183 A1* | 7/2022 | Katayama | H01L 27/14645 |

* cited by examiner

IMAGING SYSTEM AND DATA ACQUISITION METHOD AND STRUCTURE THEREOF

BACKGROUND

Field of Art

The present disclosure relates to a computer tomography (CT) scan/imaging system, and more particularly, to a data acquisition method and a data acquisition structure of a CT scan system.

Description of the Related Art

Traditionally, CT scanners use energy-integrating detectors which convert x-ray photons into a shower of visible light photons. The visible light is then incident on an underlying light sensor to generate positive and negative electrical charges. The recently developed photon counting detectors, on the other hand, do not require to convert x-ray into light, but converts the individual x-ray photons directly into an electric signal. The CT imaging system using the photon counting detectors provides higher contrast-to-noise ratio, improved spatial resolution, and optimized spectral imaging. Photon counting CT imaging system also reduces radiation exposure, reconstruct images at a higher resolution, corrects beam-hardening artifacts, optimizes the use of contrast agents, and creates opportunities for quantitative imaging relative to the traditional CT technology.

Photon counting CT imaging systems typically generates data with a rate around 80 GB/sec with many additional measurements that are made for each image pixel. In a CT imaging system, data acquisition hardware is constructed to continuously rotate around a patient. A mechanical/electric connection called a slip ring has been used to send data from the rotating portion to a console. The slip ring is an expensive component that may send data up to 4 GB/sec. While the slip ring can be reconfigured to send data at a higher rate, it is cost prohibitive to do so. To handle the high data rates, electronics for aggregating the measurements downstream to the detectors has been developed. The measurements are buffered on the rotating part of the CT gantry assembly. The buffer can be read in a variety of ways to support various cases such as streaming the data to a console in real time or read the data in a non-real-time manner after acquisition for post procedure processing.

However, as the detector field of view, that is, the number of detectors used in the photon counting CT imaging system, increases, the data rate can even reach 320 GB/sec. This becomes very challenging for the current electronic and storage design.

SUMMARY

A computer-tomography (CT) imaging system comprising an imaging data acquisition system is provided. The imaging data acquisition system comprises a plurality sets of a detector section, a storage section, and an aggregation section. The detector section includes a plurality of detector elements configured to convert radiation into electric signals. The storage section is connected with an output of the detector section and an input of the aggregation section. The storage section comprises a predetermined number of non-volatile memories to store the imaging data from the corresponding detector elements. The aggregation section is configured to aggregate imaging data carried by the electronic signals from the detector section.

Each of the detector elements may include a predetermined number of detector crystals converting X-ray photons into the electric signals. A plurality of ASICs may be used to sample the electric signals from the detector elements. The storage section may include a field programmable gate arrays (FPGA) connected to the detector elements via the ASICs. The FPGAs is connected with a predetermined number of the non-volatile memories and controls the detector elements as PCIe devices. The storage section may control the detector section and the memories as NVME-interface devices. The storage section may further be programmed in parallel by multicasting PCIe commands to trigger the detector elements to collect simultaneously. The non-volatile memories may be commercial off the shelf memories and are removable from the imaging acquisition system. The aggregation section comprises a plurality of PCIe switches arranged in a tree topology.

The storage section may be integrated within the detector section. In another embodiment, the detector section, the storage section, and the aggregation section are in the form of three separate modules. Or alternatively, the storage sections may also be integrated within the aggregation sections.

The CT imaging system further comprises a slip ring connecting a rotating portion and a stationary portion of the CT imaging system. The detector sections, the storage sections, and the aggregation sections are arranged in the rotating portion. A pair of PCIe buses may be arranged across the slip ring. The CT imaging system further comprises a process computer to process data transmitted from the aggregation sections via the slip ring. The data process computer may comprise a file system configured to directly access any one set of the detector sections, the storage sections, and the aggregation sections. In one embodiment, the file system is configured to simultaneously access a predetermined number sets of the detector sections, the storage sections, and the aggregation sections.

A radiation imaging system comprising a rotating portion and a non-rotating portion is provided. The rotating portion comprises a radiation source configured to generate radiation to be incident on an object, a detector device configured to detect radiation from the object, a storage device configured to store image data generated from the detector device; and an aggregator configured to aggregate the imaging data from the storage device. The non-rotating portion comprises a process computer to process imaging data transmitted from the rotating portion. The radiation imaging system further comprises a slip ring configured to transmit the imaging data between the rotating portion and the non-rotating portion. The storage device includes a plurality of removable non-volatile memories arranged at an output of the detector device and an input of the aggregator. In addition, the detector device may include a plurality of detector elements, and each detector element is connected with at least one corresponding non-volatile memory, such that the imaging data of each of the detector element can be stored individually.

The radiation imaging system uses a single photon counting or a non-photon counting detector module has the capability to store the data generated by multiple scans with the commercial off the shelf removable storage technology. The aggregator is able to present at least one storage and detector module as a single data source or device in the system. The aggregator may be present anywhere between the detector and the slip ring communication link. The slip ring is configured to relay packets from one PCIe bus to another PCIe bus across the slip right. The radiation imaging system further comprises a file system logically mounted on the module of the detector device, the storage device, and the aggregator to allow standard file input/output (I/O) to and from the detector device as a single volume. The file system further allows individual module of the detector device, the storage device, and the aggregator to be accessed using standard file I/O.

A method of acquiring computer-tomography (CT) imaging data is provided. CT imaging data of an object are generated by a plurality of detector elements at a rotating side of a CT imaging apparatus. At least one non-volatile memory is provided to each of the detector elements at the rotating side. The CT imaging data from each of the detector elements are stored into the corresponding non-volatile memory. The CT imaging data stored in the non-volatile memory of each of the detector element are combined into aggregated imaging data at the rotating side. The aggregated CT imaging data are then transmitted across a slip ring of the CT imaging apparatus to a stationary side of the CT imaging apparatus.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

So that features and advantages can be understood in details, a more particular description of embodiments of the invention may be had by reference to the embodiments illustrate in the appended drawings. It is to be noted, however, that the appended drawings only illustrate typical embodiments of the invention and are therefore not to be considered limiting of its scope, for the invention may admit to other equally effective embodiments.

DETAILED DESCRIPTION

The present disclosure is described in further detail below with reference to accompanying drawings and specific embodiments.

Figure 1:
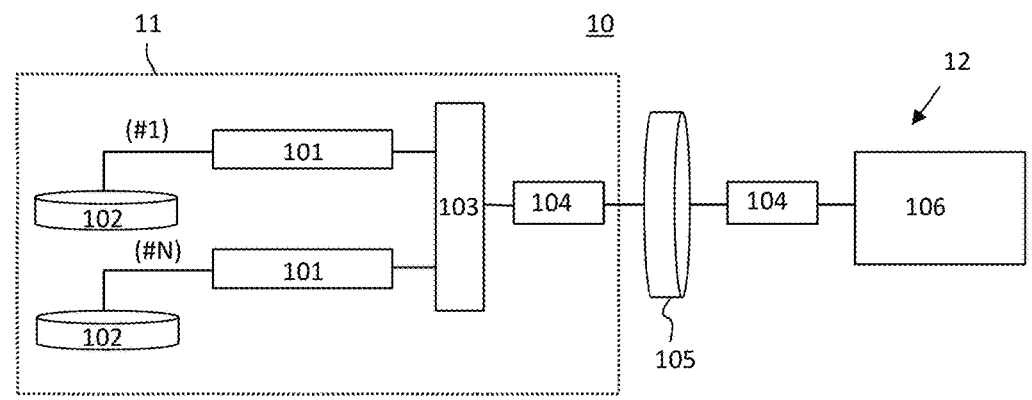
FIG. 1 is a schematic diagram of an imaging acquisition structure according to one embodiment of the current disclosure.

The CT imaging system typically includes a gantry, which may include a rotating portion framed with an X-ray source and a detector array, and a stationary (non-rotating) portion. The X-ray emits X-ray beams incident on an object to be inspected. The X-ray beams traveling through the object are attenuated thereby and then received by the detector array. The detector array converts the photons of the attenuated X-ray beams into electric signals to be processed and analyzed for diagnose. The imaging data carried by the electric signals may be acquired and processed by an imaging data acquisition structure as shown in FIG. 1. As shown, the imaging data acquisition structure 10 includes a portion located in the rotating portion 11 of a gantry and another portion in the non-rotating portion 12. An array of detectors 101 (#1) to (#N) are located in the rotating portion 11 to detect the X-ray beams from the object. Each of the detectors 101 (#1) to (#N) is connected with a corresponding memory 102 ((#1) to (#N)). To eliminate high data rates, non-volatile memories are used in the current embodiment. As each detector element, that is, imaging detector 101, contributes a small fraction of the aggregate data rate, the storage can be designed to accommodate the lower data rate from an individual detector 101; or alternatively, a small group of detectors (see FIG. 2). The memories 102 may be selected from commercial off the shell storage components. For example, non-volatile storage technology used in the current embodiment may be flash-based, CFExpress, SDEpress, or XFMExpress form factors and NVME access protocols. These form factors are very small with high G-load tolerance while used in a rotating environment. Each of the non-volatile storage capacity for each imaging detector may store multiple scans, for example, the scans performed in a day with the current storage technology. The bandwidth of each of the memories 102 is about 1 to 2 GB/sec, for example. The data imaging acquisition structure 10 further includes an aggregation and control device 103 to aggregate the imaging data from the array of detectors 101. The aggregation and control device 103 may be configured to handle a data rate at 80 GB/sec, for example. The imaging data aggregated by the aggregation and control device 103 is transmitted via a slip ring 105 with a bandwidth about 4 GB/sec. The imaging data is then transmitted from the slip ring 105 to a data process and display computer 106. In the embodiment as shown in FIG. 1, a bridge 104 is used across the slip ring 105.

Figure 2:
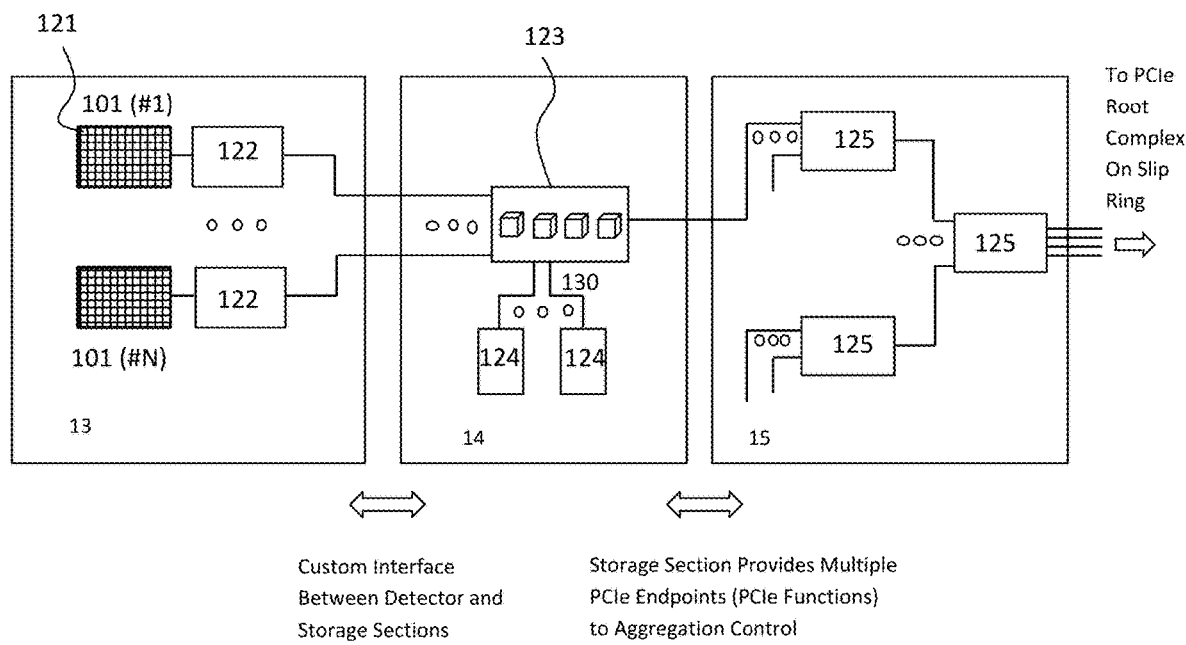
FIG. 2 is a block diagram of logic architecture of an imaging acquisition structure according to one embodiment of the current disclosure.

FIG. 2 is a block diagram of logic architecture of an imaging data acquisition structure used in the photon counting CT imaging system according to one embodiment. In FIG. 2, each block may represent a semiconductor chip or circuitry which provides the desired functionalities, while each cube may represent a firmware. The imaging data acquisition structure in the rotating portion 11 may be divided into three sections, including a detector section 13, a storage section 14, and an aggregation section 15. Each imaging detector 101 may be formed by a number or an array of detector crystals 121. The crystals 121 convert X-ray photons into electric signals. The electric signals from each imaging detector 101 are sampled by an ASIC 122 connected thereto. The ASIC's ASICs 122 may be configured to perform any selected imaging corrections and/or calibrations to the samples. As shown in FIG. 2, the circuitry uses PCIe (peripheral component interface express) or other communication standards to move the samples off the ASIC 122. The imaging data from a small number of ASICs 122 are aggregated into the storage section 14 implemented with an FPGA (field programmable gate array) 123 attached with arrays of storage devices or memories 124. The FPGA 123 may include firmware and software that represent the storage section 14 and detector section 13 as PCIe device functions. This allows the entire detector section 13 to be controlled as an array of PCIe devices which store and read acquired detector data from the detectors 101 and control the ASICs 122. Therefore, in the example as shown in FIG. 2, the interface between the FPGA 123 and the storage devices 124 includes PCIe interface 130.

Figure 3:
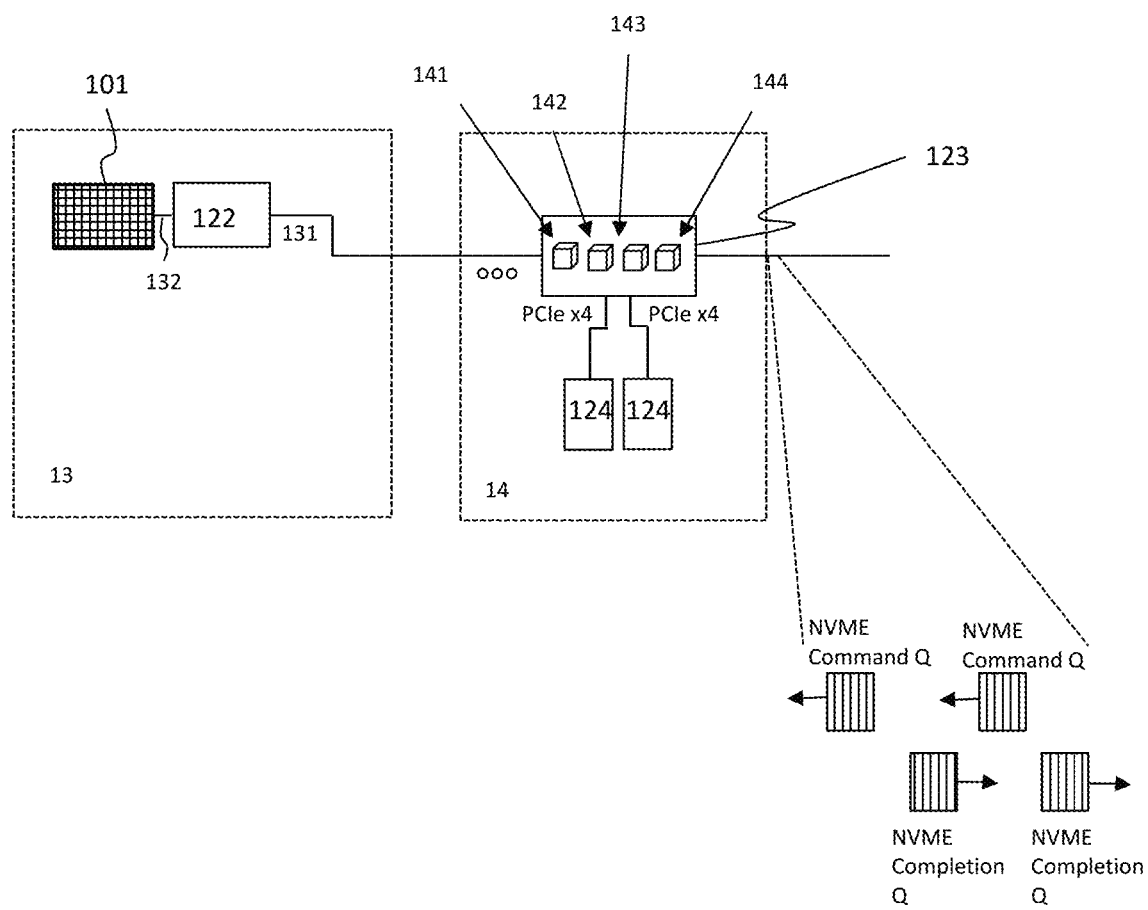
FIG. 3 is a block diagram showing the operation between the detector section and the storage section of an imaging data acquisition structure according to one embodiment of the current disclosure.

FIG. 3 shows the interface between the detector section 13 and the storage section 14 and the operation of the storage section 14. In the example as shown, bump bonds 132 are used to connect the detectors (detector elements) 101 and the corresponding ASIC 122, and ASIC input/output 131 is between the ASIC 122 and the FPGA 123. In addition to the bump bonds, other types of connections such as wire bonds can also be used between the detectors 101 and the ASIC 122. As discussed above, the FPGA 123 may be implemented with firmware and software to represent the detector section and the storage section as PCIe devices. The FPGA 123 may include various blocks, that is, reusable cells or units of logic, or integrated circuit (IC) layout designs arranged for specific purpose. For example, in FIG. 3, the FPGA 123 includes an ASIC interface block 141 to interface with the ASIC 122, a NVMe input/output block 142 for input/output of NVME, a compression block 143 for data compression and/or decompression, and a PCIe interface block 144 for PCIe interface. The FPGA 123 may use hard, soft, or firm Intellectual Property (IP) cores to implement the various blocks. In the current embodiment, the PCIe interface between the FPGA 123 and the array of memories 124 include 4 communication lanes (PCIex4).

To perform IO, an application sends read/write commands to the NVME storage device. The commands specify the type of IO, source, and destination address, for example. As shown in FIG. 3, the NVME storage device receives an IO command from an area, namely, a Command queue (Q), in the memory of a computer. Upon finish executing the IO command, a notification is placed in a Completion Q located in the NVME storage device. The NVME standard allows a device to have multiple command/completion Q pairs, one completion Q for every Command Q, so as to serve multiple commands in parallel from potentially multiple source.

The storage section uses commercial removable storage interfaced with the NVME protocol because of the ubiquity of the NVME in the market and performance. In this manner, the FPGA 123 presents both the ASICs 122 and the storage devices 124 as NVME devices with several unique namespaces. For example, ASIC namespaces contain a single logical block that contains the status and control bits of the ASICs 122 within well-known bit fields. Using the NVME 10, writing the block sets control bits and reading the block returns the current state of the ASIC. ASIC control fields can be defined to specify 10 targets within the storage namespace so that an ASIC command initiates collection to storage. Storage namespaces contain all addressable storage blocks on the storage devices. Corresponding to data collection and readout, the storage can be written by ASIC but read by "upstream" components concurrently. More description of the namespaces will be provided with reference to FIG. 7.

Figure 4:
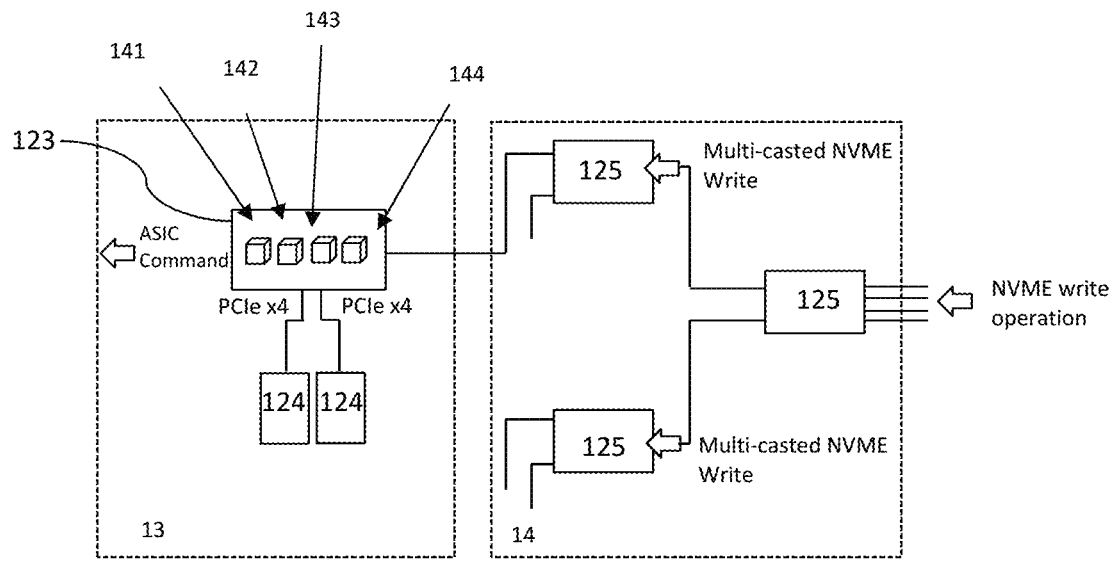
FIG. 4 is a block diagram showing the operation between the storage section and the aggregation section of an imaging data acquisition structure according to one embodiment of the current disclosure.
Figure 5A:
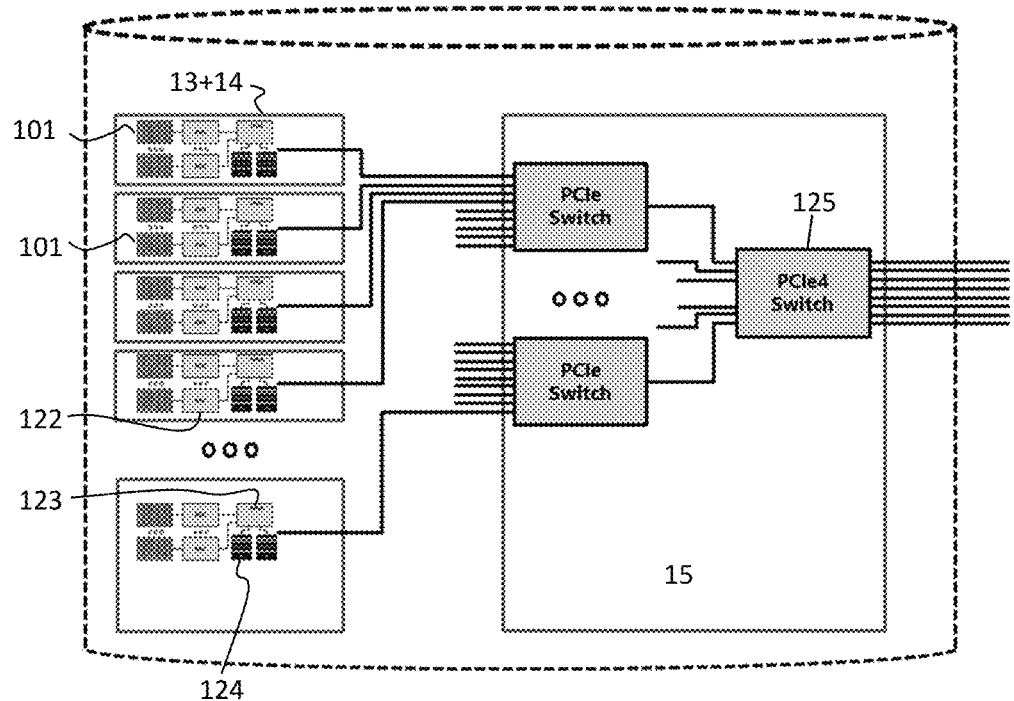
FIGS. 5A to 5C are schematic diagrams showing various layouts of the storage devices in the imaging data acquisition apparatus according to one embodiment of the current disclosure.
Figure 5B:
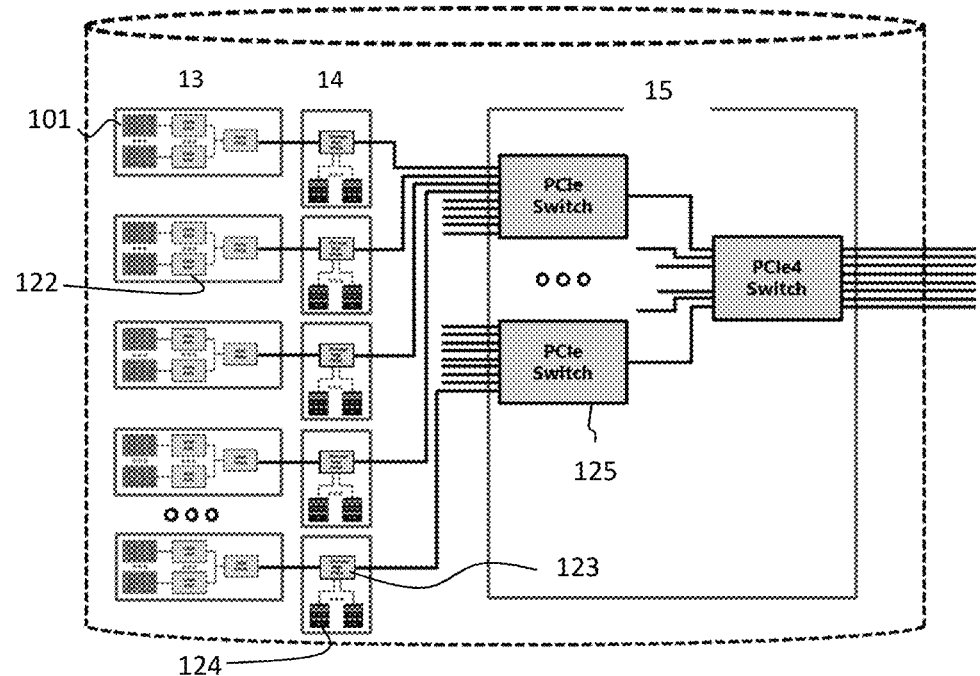

The aggregation section combines data transfers from each storage section corresponding to a predetermined number of detector crystals and routes it to the remainder of the system. In the embodiment as shown in FIG. 2, the storage section 14 provides multiple PCIe endpoints (PCIe functions) to the aggregation section 15. The aggregation section is implemented with commercial PCIe switches 125 arranged in a tree topology. The number and size of PCIe switches 125 is chosen to minimize cost, yet support slip ring throughput. FIG. 4 shows the operation between the storage section and the aggregation section according to one embodiment of the current disclosure. In this embodiment, all storage devices can be programmed in parallel by multicasting NVME IO commands using multicast features of the PCIe protocol. This allows detector section to be triggered to collect data simultaneously without use of special hardware lines, that is, this allows in-band signaling. As shown in FIGS. 5A and 5B, the image data acquisition structure may include multiple detector sections and multiple storage sections, and each of the detector sections may further comprise one or more detector elements 101. These detector sections may also be controlled individually. The FPGA 123 and aggregation network are so designed that an NVME device interface resides within a PCIe multicast address window. The NVME IO operations to this device are in fact multicast to each individually storage section using the PCIe protocol.

The number of the storage devices in the storage section is selected to support required throughput. For example, two memories 124 are used in the storage section as shown in FIG. 2. The capacity of each storage device may be scaled by purchasing the appropriate part. Current technology ranges up to 1 TB per part where only 64 GB per device might be required for a single scan. This means that a single memory used in all detector modules allow the entire system to store about 16 scans before the parts have to be read out in order to perform another scan (in practice, storage is read out continuously during and after acquisition to prevent the part from being filled).

Figure 5C:
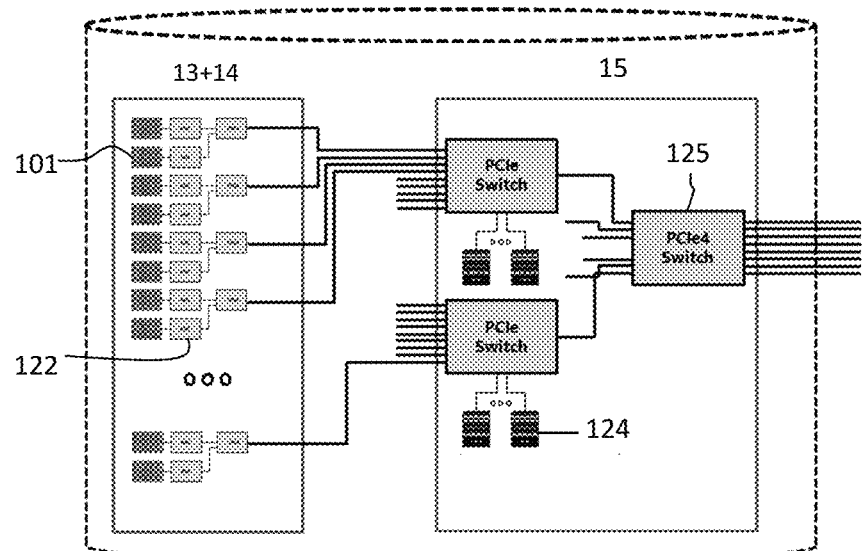

FIGS. 5A to 5C are diagrams of various embodiments in which the storage units are integrated to different positions of the imaging data acquisition structure. For example, in FIG. 5A, the storage capability, that is, at least one of multiple storage sections 14, is integrated within the corresponding detector section 13. The memories are integrated into each detector section, while multiple detector sections are connected to a common PCIe switch 125. This optimizes throughput from the detector elements. However, this might be relatively difficult to implement due to power and thermal restrictions within the detector section. In the embodiment as shown in FIG. 5B, the storage capability is integrated in its own detector section, which is physically independent of either the detector or the aggregation electronics, but stores the imaging data prior to aggregation. The separate section allows larger and wider variety of storage devices to be used in the system. However, the larger devices may mean less High-G tolerance. In FIG. 5C, the storage capability is in the front end of the aggregation electronic, that is, the end facing the detector to allow storage of imaging data prior to aggregation. Depending on ASIC-to-FPGA fan-in within the detector modules and the aggregation network that is used, this may require storage to support higher throughput. NVME storage may be directly connected to the PCIe switches 125 to simplify the design. Similar to the embodiment as shown in FIG. 5C, this may allow larger and wider variety of storage devices, which on the other hand, has less High-G tolerance.

In any of the layouts as shown in FIG. 5A to 5C, the storage section is arranged to store the imaging data from the detector section prior to the aggregation process performed in the aggregation section. That is, the imaging data are output from the storage section into the aggregation section.

Figure 6:
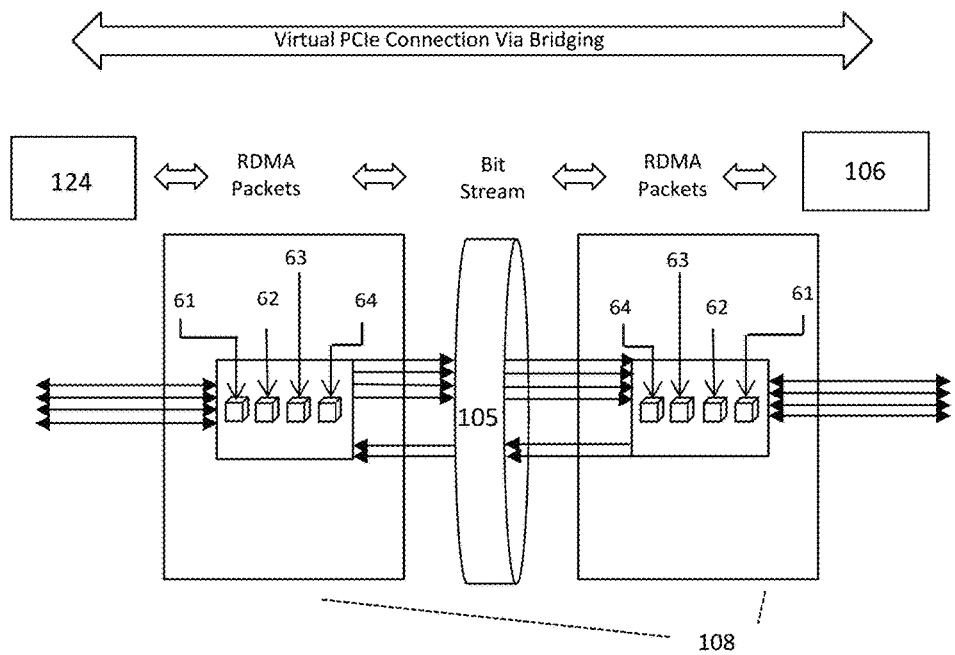
FIG. 6 is a schematic diagram of the slip ring connected between the non-rotating portion and the rotating portion of the radiation imaging system.

FIG. 6 is a schematic diagram showing the slip ring that connects the rotating portion and the stationary portion of the CT imaging system. As shown, the rotating portion and the stationary portion of a CT imaging system with a PCIe-to-PCIe bridge (104 as shown in FIG. 1) across the slip ring. The slip ring 105 functions as a PCIe-to-PCIe bridge to relay PCIe programmed input/output (PIO) or direct memory access (DMA) between the rotating portion and the stationary portion. This makes all components on the rotating portion appear as local PCIe endpoints to the real-time computer on the stationary side. Remote direct memory access (RDMA) is a direct memory access from the memory of one computer into the memory of another computer without involving the operating system of either computer. Therefore, in the embodiment as shown in FIG. 6, RDMA packets are transmitted between the of rotational side and the stationary side. The entire packets are forwarded (transmitted in bit stream) across the slip ring. The system and the gantry electronics are independent with each other. The devices are mirror imaged at two opposite sides of the slip ring. Data for transmission across the slip ring may be compressed, while the received data may be decompressed. In FIG. 6, the slip ring differences, for example, allocation of upstream and downstream lanes can be hidden. In addition, the bridge between the PCIe buses can be either transparent and non-transparent. In the embodiment as shown in FIG. 6, the compression and decompression are only assigned to the slip ring interface. Therefore, if a new or existing computer is used to access and manipulate the data stream, the access or manipulation can be performed directly without the need to decompress the data first. In FIG. 6, the FPGA of the PCIe bridge may include various Intellectual Property cores such as a PCIe IP 61, a RDMA IP 62, a Compression IP 63, and a Schliefring TX/RX IP 64 for PCIe interface, RDMA transmission, data compression and/or decompression, and data transmission across the slip ring, respectively.

Figure 7:
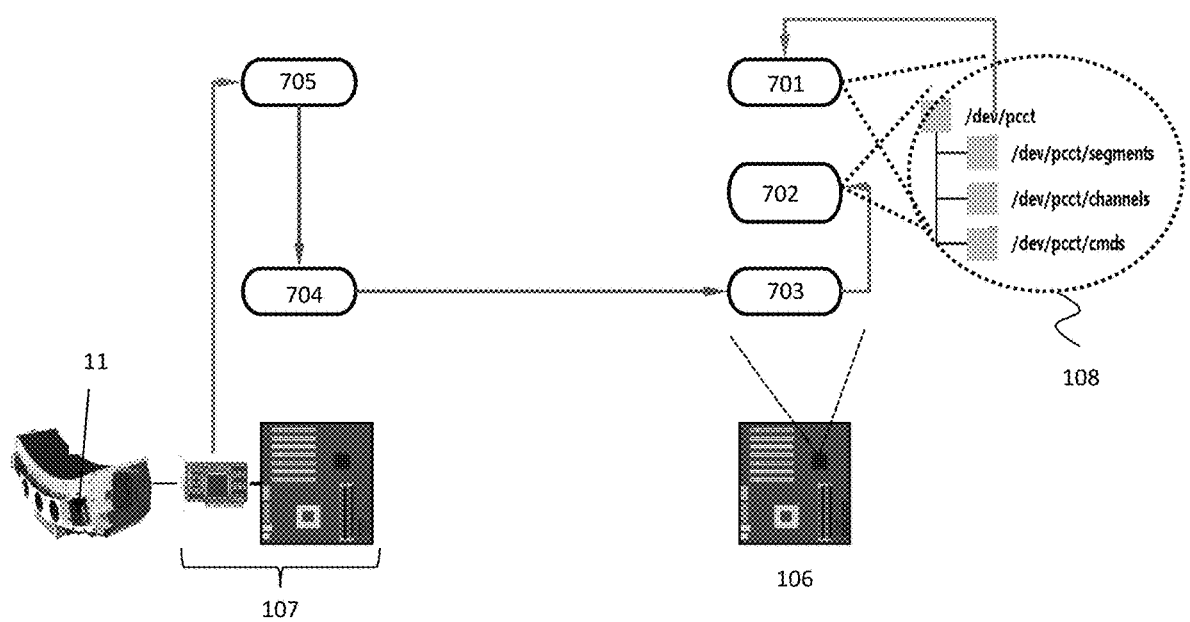
FIG. 7 is a schematic diagram of a file system flow diagram in which data are transmitted from CT computer to detector.

In addition to the various physical layouts of the detector section and storage section as shown in FIG. 5A to FIG. 5C, the arrangements of the detectors in the detector section may also implemented by a file system. FIG. 7 shows an exemplary file system which uses software to model detector functions and storage. The file system may be a standard POSIX file system which provides bi-directional communication between the rotational portion and the stationary portion of the CT system. For communication from the CT computer in the stationary portion to the rotational portion, an application software 701 uses standard I/O operations to access a local file, for example, open( ), read( ), write( ), and close( ). The operating system driver (kernel module) 702 re-routes the I/O request across the slip ring to the detector software 704. The detector software 704 may run on the computer 107 on the rotational side to access portion of detector storage corresponding to the I/O request. In the example as shown in FIG. 7, through libnvme (linux) 705, the NVME physical I/O read/write request is issued to correct detector storage module. Libnvme is an open source library that provides type definitions for NVMe specification structures, enumerations, and bit fields, helper functions to construct, dispatch, and decode commands and payloads, and utilities to connect, scan, and manage NVMe devices on a Linux system. For the communication from the detector to the CT computer, I/O data is returned to the rotation side computer 107 from the detector. The I/O data is transmitted to the detector software 704, via which the detector data is sent across the slip ring to the file system driver 703. The file system driver 703 receives I/O data and relays to application. The operating system 702 performs data copy from the file system driver 703 to the application buffer. The application software 701 receives results from I/O operations, for example, open( ), read( ), write( ), and close( ).

In FIG. 7, the file system includes a namespace, which is a directory hierarchy of the file system visible to software running on the computer 106. On a Linux system, the namespace can be used to represent various objects. For example, the file system namespace represents the arrangement of files on a disk. One can use simple file IO operations and make these IO operations mean different things depending on which portion of the namespace is accessed under Linux. For example, one can apply this to the storage detector by modifying Linux so that a certain portion of the namespace represents data stored on the detector. The namespace area used in the example as shown in FIG. 7 is named "/dev/pcct." When an application need data from the detector, the application may simply open what appears to be a file "/dev/pcct/segments" and read from it.

Figure 8:
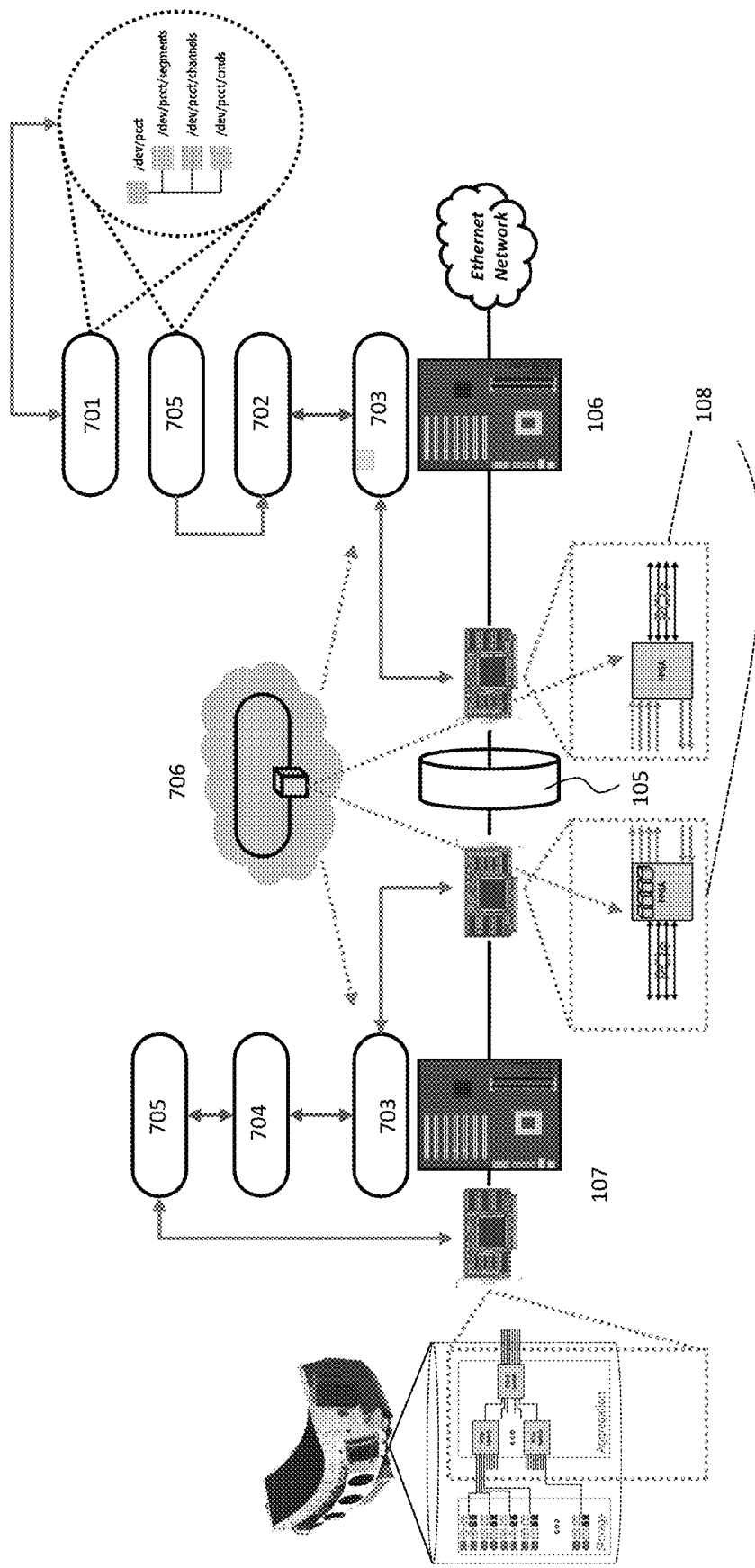
FIG. 8 is a schematic diagram of a file system flow diagram in which data are transmitted from detector to CT computer.

FIG. 8 shows the CT system using the storage-detector as a file system. The software models detector functions and storage as the file system in standard UNIX practice, for example. In the embodiment, libnvme 705 is used in both rotational portion and the stationary portion to mount the file system to the CT system. In this embodiment, Xillybus is used as the file system driver 703 at both the rotational portion and the stationary of the CT system, the possible approach to bridge implementation with OTS tech uses Xillybus IP and software drivers 706. It is appreciated that Xillybus is only an example. The implementation can also be achieved with an FPGA and associated firmware. The file system may select the imaging data received from a selected one or group of pixels of a selected group of detector modules to be transmitted from the corresponding storage devices. In this way, detector implementation details and geometry can be hidden, and the applications can be simplified. The aggregation of data, control signals, and status may also be bypassed to permit direct addressing of an individual detector through the same file system. By selecting the imaging data received from a selected group of pixels. Any additional policies that access detector data can be modelled with the creation of new files using the same method.

Figure 9:
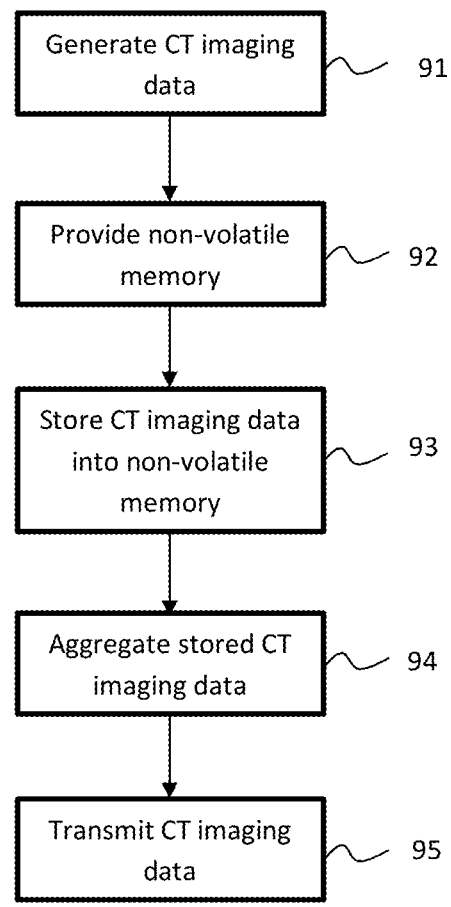
FIG. 9 is a flow chart of a method for acquiring CT imaging data using the data acquisition structure as shown in FIGS. 1-8.

In the structures as shown in FIGS. 1 to 6, non-volatile storage may be made a part of the imaging detector itself. Since each imaging detector contributes only a small fraction of the aggregate data rate, the storage can be designed to accommodate the lower data rate from an individual detector or small groups of detectors. With such structure, CT imaging apparatus can handle a much higher data rate without increasing the load and cost of the slip ring. FIG. 9 shows a process flow of a CT imaging data acquisition method that uses this structure. In step S91, CT imaging data are generated by a detector section at a rotating side of a CT imaging apparatus. The detector section may include multiple detector elements. Each of the detector elements is provided with at least one non-volatile memory in step S92, so that the CT imaging data of each detector element can be stored in the corresponding non-volatile memory in step S93. In step S94, the data from each of the non-volatile memories are combined, that is, aggregated and the transmitted to the other side of the CT imaging apparatus across a slip ring.

Further modifications and alternative embodiments of various aspects will be apparent to those skilled in the art in view of this description. Accordingly, this description is to be construed as illustrative only. It is to be understood that the forms shown and described herein are to be taken as examples of embodiments. Elements and materials may be substituted for those illustrated and described herein, parts and processes may be reversed, and certain features may be utilized independently, all as would be apparent to one skilled in the art after having the benefit of this description.

What is claimed is:

1. A computer-tomography (CT) imaging system, comprising:
    an imaging data acquisition structure, comprising:
        a detector section comprising a plurality of detector elements configured to convert radiation into electric signals that carry imaging data;
        an aggregation section configured to aggregate the imaging data carried by the electric signals from the detector section; and
        a storage section arranged at an output of the corresponding detector section and an input of the aggregation section, wherein the storage section comprises a plurality of non-volatile memories configured to store the imaging data from the detector elements, wherein each non-volatile memory of the plurality of non-volatile memories is configured to simultaneously store the imaging data of multiple images from a respective one or more of the plurality of detector elements.

2. The CT imaging system according to claim 1, wherein each of the detector elements includes a predetermined number of detector crystals converting X-ray photons into the electric signals.

3. The CT imaging system according to claim 1, wherein each non-volatile memory of the plurality of non-volatile memories is configured to simultaneously store imaging data from a plurality of scans, and wherein each scan of the plurality of scans includes a respective plurality of images.

4. The CT imaging system according to claim 1, wherein the storage section includes control circuitry that is connected to the detector section and to the aggregation section, and
    wherein the plurality of non-volatile memories communicate with the detector section and the aggregation section only through the control circuitry.

5. The CT imaging system according to claim 4, wherein the control circuitry include an FPGA.

6. The CT imaging system according to claim 4, wherein the control circuitry is configured to control the detector elements as PCIe (peripheral component interconnect express) devices.

7. The CT imaging system according to claim 4, wherein the detector section and the aggregation section communicate with each other only through the control circuitry.

8. The CT imaging system according to claim 7, wherein the control circuitry controls the detector elements and the plurality of non-volatile memories as NVME (non-volatile memory express)—interface devices.

9. The CT imaging system according to claim 8, wherein the storage section is programmed in parallel by multicasting PCIe IO (input/output) commands to trigger the detector elements to collect simultaneously.

10. The CT imaging system according to claim 1, wherein the aggregation section comprises a plurality of PCIe switches arranged in a tree topology.

11. The CT imaging system according to claim 1,
    wherein each non-volatile memory stores the imaging data from only one respective detector element of the plurality of detector elements,
    wherein the plurality of non-volatile memories are physically separated from each other, and
    wherein the aggregation section and the storage section are configured to control access to the plurality of non-volatile memories as a single logical memory.

12. The CT imaging system according to claim 11, further comprising:
    a slip ring connecting a rotating portion and a stationary portion of the CT imaging system; and
    a process computer arranged in the stationary portion and configured to process data transmitted from the aggregation section, wherein the process computer and the aggregation section communicate across the slip ring,
    wherein the detector section, the storage section, and the aggregation section are arranged in the rotating portion, and
    wherein the process computer accesses the plurality of non-volatile memories across the slip ring as a single logical memory via the aggregation section and the storage section.

13. The CT imaging system according to claim 1, wherein the storage section is integrated within the aggregation section.

14. The CT imaging system according to claim 1, further comprising a slip ring connecting a rotating portion and a stationary portion of the CT imaging system.

15. The CT imaging system according to claim 14, wherein the detector section, the storage section, and the aggregation section are arranged in the rotating portion.

16. The CT imaging system according to claim 15, further comprising a pair of PCIe buses across the slip ring.

17. The CT imaging system according to claim 16, further comprising a process computer to process data transmitted from the aggregation section, wherein the process computer and the aggregation section communicate via the pair of PCIe buses across the slip ring.

18. The CT imaging system according to claim 17, wherein the process computer further comprises a file system configured to directly access the detector section, the storage section, and the aggregation section via the pair of PCIe buses across the slip ring.

19. The CT imaging system according to claim 18, further comprising a plurality of detector sections and a plurality of storage sections, wherein the file system is configured to simultaneously access a predetermined number of the detector sections, the storage sections, and the aggregation section via the pair of PCIe buses across the slip ring.

20. A radiation imaging system, comprising:
    a rotating portion, comprising:
        a radiation source configured to generate radiation to be incident on an object;
        a detector device comprising a plurality of detector elements configured to detect radiation from the object and generate imaging data based on the detected radiation;
        a storage device configured to store the imaging data generated by the detector device; and
        an aggregator configured to aggregate the imaging data from the storage device;

a non-rotating portion, comprising a process computer to process imaging data transmitted from the rotating portion; and a slip ring configured to transmit the imaging data between the rotating portion and the non-rotating portion, wherein the storage device includes a plurality of non-volatile memories arranged at an output of the detector device and an input of the aggregator, wherein during a scan the rotation portion rotates around the object and each detector element of the plurality of detector elements generates respective imaging data for multiple images, wherein each non-volatile memory of the plurality of non-volatile memories is configured to simultaneously store the respective imaging data for the multiple images that were generated by a respective one or more detector elements of the plurality of detector elements.

21. The radiation imaging system according to claim 20, wherein the storage device includes control circuitry that is connected to the detector device, and wherein the plurality of non-volatile memories communicate with the detector device only through the control circuitry.

22. A method of acquiring computer-tomography (CT) imaging data, comprising:

while rotating a rotating side of a CT imaging apparatus around an object, generating CT imaging data for multiple images of the object by a plurality of detector elements on the rotating side of a CT imaging apparatus;

providing, at the rotating side, a plurality of non-volatile memories that are in communication with the detector elements at the rotating side;

simultaneously storing, in each non-volatile memory of the plurality of non-volatile memories, the CT imaging data for the multiple images from a respective one or more of the plurality of detector elements;

combining the CT imaging data stored in the plurality of non-volatile memories into aggregated imaging data at the rotating side; and transmitting the aggregated CT imaging data across a slip ring of the CT imaging apparatus to a stationary side of the CT imaging apparatus.

* * * * *